United States Patent [19]

Conn et al.

[11] 4,329,532

[45] May 11, 1982

[54] PROCESS FOR THE PREPARATION OF AROMATIC HYDROCARBON MIXTURE

[75] Inventors: Paul J. Conn, Houston, Tex.; Martin F. M. Post, Amsterdam, Netherlands

[73] Assignee: Shell Oil Company, Houston, Tex.

[21] Appl. No.: 128,416

[22] Filed: Mar. 10, 1980

[30] Foreign Application Priority Data

Mar. 14, 1979 [NL] Netherlands .................. 7902019

[51] Int. Cl.$^3$ ........................................ C10G 35/095
[52] U.S. Cl. ............................... 585/407; 208/135; 585/415
[58] Field of Search ............... 585/407, 415; 208/135

[56] References Cited

U.S. PATENT DOCUMENTS

| | | | |
|---|---|---|---|
| 3,756,942 | 9/1973 | Cattanach | 585/407 |
| 3,760,024 | 9/1973 | Cattanach | 585/415 |
| 3,775,501 | 11/1973 | Kaeding et al. | 585/414 |
| 3,843,740 | 10/1974 | Mitchell et al. | 585/412 |
| 3,845,150 | 10/1974 | Yan et al. | 208/135 |
| 3,890,218 | 6/1975 | Morrison | 208/135 |
| 3,894,103 | 7/1975 | Chang et al. | 208/135 |
| 3,926,782 | 12/1975 | Plank et al. | 208/135 |
| 3,960,978 | 6/1976 | Gikens et al. | 585/531 |
| 4,105,541 | 8/1978 | Plank et al. | 208/111 |
| 4,113,788 | 9/1978 | Kaeding et al. | 585/415 |
| 4,180,689 | 12/1979 | Davies et al. | 585/407 |

*Primary Examiner*—Delbert E. Gantz
*Assistant Examiner*—G. E. Schmitkons

[57] ABSTRACT

An improved process is disclosed for the preparation of aromatic hydrocarbon mixture from monoolefins having not more than four carbon atoms by contacting with certain crystalline silicate catalysts having certain ratio of composition to crystallite size to achieve durable selectivity.

3 Claims, No Drawings

PROCESS FOR THE PREPARATION OF AROMATIC HYDROCARBON MIXTURE

BACKGROUND OF THE INVENTION

The invention relates to a process for the preparation of an aromatic hydrocarbon mixture from a monoolefin with at most 4 carbon atoms in the molecule (a $C_{4-}$ monoolefin) or from a hydrocarbon mixture which consists of more than 75%w $C_{4-}$ monoolefins, using a certain crystalline silicate as the catalyst.

In an investigation by the applicants concerning the above-mentioned process it has been found that the aromatics selectivity and the change of this selectivity of these catalysts with time are in the first place greatly dependent on the value of y in the formula appearing hereinafter, where y is the alumina to silica ratio, which gives the overall composition of the silicate, and further on the average crystallite size (d) of the silicate. It was ascertained that to reach an aromatics selectivity and a change of this selectivity with time which are acceptable for commercial use of the process, y should be at least 0.0030 and at most 0.0075, and d at most 500 nm.

SUMMARY OF THE INVENTION

The present invention therefore relates to a process for the preparation of an aromatic hydrocarbon mixture, in which a $C_{4-}$ monoolefin or a hydrocarbon mixture which consists of more than 75%w $C_{4-}$ monoolefins is contacted with a crystalline silicate as defined above as the catalyst, in which in the formula which gives the overall composition of the silicate the value of y is at least 0.0030 and at most 0.0075 and in which the silicate has a d of at most 500 nm.

DESCRIPTION OF PREFERRED EMBODIMENTS

In the process according to the invention the starting material should be a $C_{4-}$ monoolefin or a hydrocarbon mixture which consists of more than 75%w $C_{4-}$ monoolefins. Eligible $C_{4-}$ monoolefins are ethene, propene, butene and isobutene. If the starting material is a hydrocarbon mixture which comprises in addition to one or more $C_{4-}$ monoolefins one or more other hydrocarbons, among these other hydrocarbons may be paraffins, diolefins or $C_{5+}$ monoolefins. The preferred starting material is a $C_3$ or $C_4$ monoolefin or a hydrocarbon mixture substantially comprising one or more of these monoolefins. A very suitable feed for the present process is a hydrocarbon mixture substantially consisting of $C_3$ and/or $C_4$ monoolefins which has been obtained as by-product in the catalytic or thermal cracking of hydrocarbons, in particular in the thermal cracking of hydrocarbons for the preparation of ethylene.

The process according to the invention is preferably carried out at a temperature from about 350° to 550° C. and particularly from about 400° to 500° C., a pressure from about 3 to 20 bar and particularly from about 5 to 15 bar and a space velocity from about 1-20 $g.g^{-1}.h^{-1}$ and particularly from about 2-10 $g.g^{-1}.h^{-1}$. If desired, the process may be carried out in the presence of hydrogen.

In the process according to the invention a $C_{4-}$ monoolefin or a hydrocarbon mixture which consists of more than 75%w $C_{4-}$ monoolefins, and particularly a $C_3$ or $C_4$ monoolefin or a hydrocarbon mixture which consists substantially of one or more of these monoolefins, is converted into an aromatic hydrocarbon mixture by contacting this feed with certain crystalline silicates.

These crystalline silicates are characterized in that they have the following properties after 1 hour's calcining in air at 500° C.:

(a) thermally stable up to a temperature above 600° C., (b) an X-ray powder diffraction pattern showing, inter alia, the reflections given in Table A.

TABLE A

| Radiation: Cu—Kα 2θ | Wavelength 0.15148 nm relative intensity |
|---|---|
| 7.8–8.2 | S |
| 8.7–9.1 | M |
| 11.08–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M | wherein the letters used have the following meanings:

VS=very strong; S=strong; M=moderate; W=weak; θ=angle according to Bragg's law, (c) after conversion of the silicate into the H-form and after evacuation at $2 \times 10^{-9}$ bar and 400° C. for 16 hours and measured at a hydrocarbon pressure of $8 \times 10^{-2}$ bar and 100° C., the adsorption of n-hexane is at least 0.8 mmol/g, the adsorption of 2,2-dimethylbutane is at least 0.5 mmol/g and the ratio $$\frac{\text{adsorption of n-hexane}}{\text{adsorption of 2,2-dimethylbutane}} \text{ at least } 1.5,$$

(d) the composition expressed in moles of the oxides is as follows:

$y.(1.0 \pm 0.3)M_{n/2}O.y.Al_2O_3.SiO_2$, wherein M=H and/or alkali metal and/or alkaline-earth metal, n is the valency of M, and $0 < y \leq 0.1$.

For the adsorption measurements mentioned under (c) the silicate should first be converted into the H-form. This conversion is effected by boiling the silicate calcined at 500° C. with 1.0 molar $NH_4NO_3$ solution, washing with water, boiling again with 1.0 molar $NH_4NO_3$ solution and washing, drying at 120° C. and calcining at 500° C.

The complete X-ray powder diffraction pattern of a typical example of a silicate eligible for use according to the invention is shown in Table B (radiation: Cu-Kα; wavelength: 0.15418 nm).

TABLE B

| 2θ | relative intensity (100. $I:I_o$) | description |
|---|---|---|
| 8.00 | 55 | SP |
| 8.90 | 36 | SP |
| 9.10 | 20 | SR |
| 11.95 | 7 | NL |
| 12.55 | 3 | NL |
| 13.25 | 4 | NL |
| 13.95 | 10 | NL |

TABLE B-continued

| 2 θ | relative intensity (100. I:I_o) | description |
|---|---|---|
| 14.75 | 9 | BD |
| 15.55 | 7 | BD |
| 15.95 | 9 | BD |
| 17.75 | 5 | BD |
| 19.35 | 6 | NL |
| 20.40 | 9 | NL |
| 20.90 | 10 | NL |
| 21.80 | 4 | NL |
| 22.25 | 8 | NL |
| 23.25 | 100* | SP |
| 23.95 | 45 | SP |
| 24.40 | 27 | SP |
| 25.90 | 11 | BD |
| 26.90 | 9 | BD |
| 27.50 | 4 | NL |
| 29.30 | 7 | NL |
| 29.90 | 11 | BD |
| 31.25 | 2 | NL |
| 32.75 | 4 | NL |
| 34.40 | 4 | NL |
| 36.05 | 5 | BD |
| 37.50 | 4 | BD |
| 45.30 | 9 | BD |

*$I_o$ = intensity of the strongest separate reflection present in the pattern.

The letters used in Table B for describing the reflections have the following meanings:
SP=sharp;  SR=shoulder;  NL=normal;
BD=broad; θ=angle according to Bragg's law.

The crystalline silicates which are used as the catalyst in the process according to the invention can be prepared from an aqueous mixture as the starting material which contains the following compounds:
one or more compounds of an alkali or alkaline-earth metal (M), one or more compounds containing an organic cation (R) or from which such a cation is formed during the preparation of the silicate, one or more silicon compounds and one or more aluminum compounds. Exemplary organic cations include, e.g. primary, secondary, and tertiary alkylamines and quaternary ammonium compounds. The preparation takes place by maintaining the mixture at elevated temperature until the silicate has been formed and subsequently separating the crystals of the silicate from the mother liquor. In the aqueous mixture from which the silicates are prepared the various compounds should be present in the following ratios, expressed in moles of the oxides:

$M_{2/n}O : (R)_{2/p}O = 0.1-20$,
$(R)_{2/p}O : SiO_2 = 0.01-0.5$,
$SiO_2 : Al_2O_3 = 130-600$, and
$H_2O : SiO_2 = 5-50$;

n is the valency of M and p is the valency of R.

In the preparation of the silicates it is preferred to start from a basic mixture in which M is present in a sodium compound and R in a tetrapropylammonium compound.

For the silicates which are suitable for use as the catalyst in the process according to the invention, the following holds: $0.0075 \geq \ \geq 0.0030$ and $d \leq 500$ nm. The value of y in the formula which gives the composition of the silicates can be adjusted with the aid of the molar ratio of $SiO_2$ to $Al_2O_3$ in the starting mixture, in the sense that silicates with a lower value for y are obtained according as the molar ratio of $SiO_2$ to $Al_2O_3$ in the starting mixture is chosen higher. The average crystallite size d of the silicates can be adjusted by means of the molar ratio of $(R)_{2/p}O$ to $SiO_2$ in the starting mixture, in the sense that silicates with a lower average crystallite size are obtained according as the molar ratio of $(R)_{2/p}O$ to $SiO_2$ in the starting mixture is chosen higher.

The silicate prepared in the way described above contain alkali metal ions and/or alkaline-earth metal ions and organic cations. With the use of suitable exchange methods the alkali metal ions and alkaline-earth metal ions can be replaced by other cations, such as hydrogen ions or ammonium ions. Organic cations can be very suitably converted into hydrogen ions by calcining the silicates. The crystalline silicates which are used in the process according to the invention as the catalyst preferably have an alkali metal content of less than 0.1%w and in particular of less than 0.01%w. When the crystalline silicates are used as the catalyst, they may, if desired, be combined with a binder material such as bentonite or kaolin.

The process according to the invention can very conveniently be carried out by conducting the feed in upward or downward direction through a vertically mounted reactor, in which a fixed or moving bed of the catalyst concerned is present.

The invention will now be explained with reference to the following example.

EXAMPLE

Six crystalline silicates (silicates A-F) were prepared by heating mixtures of $SiO_2$, $NaAlO_2$, NaOH and $[(C_3H_7)_4N]OH$ in water in an autoclave under autogenous pressure at 150° C. for 24 hours. After the reaction mixtures had cooled down, the silicates formed were filtered off, washed with water until the pH of the wash water was about 8 and dried for two hours at 120° C. After 1 hour's calcining in air at 500° C. the silicates A-F had the following properties.

(a) thermally stable up to a temperature above 800° C.;
(b) an X-ray powder diffraction pattern substantially equal to the one given in Table B;
(c) after conversion of the silicate into the H-form and after evacuation at $2 \times 10^{-9}$ bar and 400° C. for 16 hours and measured at a hydrocarbon pressure of $8 \times 10^{-2}$ bar and 100° C., the adsorption of n-hexane is 1.2 mmol/g, the adsorption of 2,2-dimethylbutane is 0.7 mmol/g and the ratio $$\frac{\text{adsorption of n-hexane}}{\text{adsorption of 2,3-dimethylbutane}} = 1.7;$$

(d) the composition, expressed in moles of the oxides, is the following:
silicate A: 0.0105 $M_2O$. 0.0105 $Al_2O_3.SiO_2$
silicate B: 0.0069 $M_2O$. 0.0069 $Al_2O_3.SiO_2$
silicate C: 0.0059 $M_2O$. 0.0059 $Al_2O_3.SiO_2$
silicate D: 0.0038 $M_2O$. 0.0038 $Al_2O_3.SiO_2$
silicate E: 0.0031 $M_2O$. 0.0031 $Al_2O_3.SiO_2$
silicate F: 0.002 $M_2O$. 0.002 $Al_2O_3.SiO_2$
wherein M=H and Na.

The molar composition of the aqueous mixtures from which the silicates A-F were prepared are given in Table C.

TABLE C

| Silicate | A | B | C | D | E | F |
|---|---|---|---|---|---|---|
| $Na_2O$ | 5 | 8 | 8 | 16 | 16 | 24 |
| $Al_2O_3$ | 1 | 1 | 1 | 1 | 1 | 1 |
| $[(C_3H_7)_4N]_2O$ | 22.5 | 36 | 12 | 72 | 24 | 108 |
| $SiO_2$ | 125 | 200 | 200 | 400 | 400 | 600 |

TABLE C-continued

| Silicate | A | B | C | D | E | F |
|---|---|---|---|---|---|---|
| H₂O | 2250 | 3600 | 3600 | 7200 | 7200 | 10800 |

The silicates I-VI were prepared from the silicates A-F, respectively, by boiling the materials calcined at 500° C. with 1.0 molar NH₄NO₃ solution and washing, drying at 120° C. and calcining at 500° C.

The silicates I-VI were tested as the catalyst for the preparation of an aromatic hydrocarbon mixture from isobutene. The test was carried out in a 50-ml reactor fitted with a fixed catalyst bed having a volume of 5 ml and comprising the silicate concerned. Isobutene was conducted over the catalyst at 400° C., a pressure of 10 bar, a space velocity of 3.4 g isobutene/g silicate/h and a H₂/isobutene molar ratio of 5:1. The results of these experiments are shown in Table D. The table gives:

(a) the aromatics selectivities (expressed as yield of aromatics in %w based on isobutene feed) after 1 day and after 10 days,
(b) y of the silicate used,
(c) the average crystallite size (d) of the silicate used.

TABLE D

| Experiment | 1 | 2 | 3 | 4 | 5 | 6 |
|---|---|---|---|---|---|---|
| Silicate | I | II | III | IV | V | VI |
| y | 0.0105 | 0.0069 | 0.0059 | 0.0038 | 0.0031 | 0.0020 |
| d, nm | 250 | 200 | 900 | 200 | 700 | 300 |
| aromatics selectivity after 1 day, % w | 25 | 24 | 21 | 22 | 21 | 17 |
| aromatics selectivity after 10 days, % w | 2 | 21 | 6 | 20 | 13 | 14 |

Of the experiments shown in Table D, only the numbers 2 and 4 are experiments according to the invention. The catalysts used in these experiments were silicates that satisfied the requirements concerning y and d. In these experiments both a high aromatics selectivity and a slight change of this selectivity with time were reached. The experiments 1, 3, 5 and 6 are outside the scope of the invention and have been included for comparison. In experiment 1 a silicate with too high y-value was used and in experiments 3 and 5 a silicate with too high d-value, which led to an unacceptably rapid fall of the aromatics selectivity. In experiment 6 a silicate was used with too low y-value, which resulted in an unacceptably low aromatics selectivity.

What is claimed is:

1. A process for the preparation of an aromatic hydrocarbon mixture, which comprises contacting as feed a $C_4$– monoolefin or a hydrocarbon mixture which consists of more than 75%w $C_4$– monoolefins, at temperature in the range from 350° to 550° C. and a pressure in the range of 3 to 20 bar and a space velocity from 1 to 20 $g \cdot g^{-1} h^{-1}$ in a contact zone with a catalyst consisting essentially of a crystalline silicate, which silicate is characterized by having the following properties after 1 hour's calcining in air at 500° C.:

(a) thermally stable up to a temperature above 600° C.,
(b) an X-ray powder diffraction pattern showing, inter alia, the reflections given in Table A:

TABLE A

| Radiation: Cu—Kα 2θ | Wavelength 0.15148 nm relative intensity |
|---|---|
| 7.8–8.2 | S |
| 8.7–9.1 | M |
| 11.08–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M | wherein the letters used have the following meanings:

VS=very strong; S=strong; M=moderate; W=weak; θ angle according to Bragg's law, (c) after conversion of the silicate into the H-form and after evacuation at $2 \times 10^{-9}$ bar and 400° C. for 16 hours and measured at a hydrocarbon pressure of $8 \times 10^{-2}$ bar and 100° C., the adsorption of n-hexane is at least 0.8 mmol/g, the adsorption of 2,2-dimethylbutane is at least 0.5 mmol/g and the ratio $$\frac{\text{adsorption of n-hexane}}{\text{adsorption of 2,2-dimethylbutane}} = \text{at least } 1.5,$$

(d) the composition expressed in moles of the oxides is as follows: $y.(1.0 \pm 0.3) M_{n/2} O. y. Al_2O_3.SiO_2$, wherein M=H and/or alkali metal and/or alkaline-earth metal, n is the valency of M and $0.0075 \geq y \geq 0.0030$, and (e) an average crystallite size (d) ≦ 500 nm, and withdrawing an aromatic hydrocarbon mixture product from said contact zone.

2. A process according to claim 1, wherein the feed is a $C_3$ or $C_4$ monoolefin or a hydrocarbon mixture substantially comprising one or more of these monoolefins.

3. A process according to claim 1, wherein the temperature is in the range of from 400° to 500° C., the pressure is in the range of from 5 to 15 bar and the space velocity is in the range of from 2 to 10 $g \cdot g^{-1} \cdot h^{-1}$.

* * * * *